United States Patent
Xiao et al.

(10) Patent No.: US 9,890,137 B2
(45) Date of Patent: Feb. 13, 2018

(54) 2-HALO-5-ALKYNYL-PYRIDYL NICOTINIC LIGANDS

(71) Applicant: Georgetown University, Washington, DC (US)

(72) Inventors: Yingxian Xiao, Potomac, MD (US); Kenneth J. Kellar, Bethesda, MD (US); Milton L. Brown, Brookeville, MD (US); Mikell A. Paige, Fairfax, VA (US); Yong Liu, Rockville, MD (US)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 14/780,788

(22) PCT Filed: Mar. 26, 2014

(86) PCT No.: PCT/US2014/031873
§ 371 (c)(1),
(2) Date: Sep. 28, 2015

(87) PCT Pub. No.: WO2014/160783
PCT Pub. Date: Oct. 2, 2014

(65) Prior Publication Data
US 2016/0031853 A1   Feb. 4, 2016

Related U.S. Application Data

(60) Provisional application No. 61/805,646, filed on Mar. 27, 2013.

(51) Int. Cl.
*C07D 401/12*   (2006.01)
(52) U.S. Cl.
CPC .................. *C07D 401/12* (2013.01)

(58) Field of Classification Search
CPC .... C07D 401/12; C07D 205/02; A61K 31/44; A61K 31/397
(Continued)

(56) References Cited

U.S. PATENT DOCUMENTS 5,914,328 A * 6/1999 Lin ..................... C07D 401/12
514/252.03
8,030,300 B2 * 10/2011 Kozikowski ......... C07D 471/18
514/210.2
(Continued)

FOREIGN PATENT DOCUMENTS

WO    WO-98/25920 A1    6/1998
WO    WO-2013/071097 A1   5/2013

OTHER PUBLICATIONS

Huang, X. et al., "Modeling Differential Binding of α4β2 Nicotinic Acetylcholine Receptor with Agonists and Antagonists", *J. Am. Chem. Soc.*, 130:16691-16696 (American Chemical Society, USA, 2008).
(Continued)

*Primary Examiner* — Daniel Carcanague
(74) *Attorney, Agent, or Firm* — Foley Hoag LLP

(57) ABSTRACT

Disclosed are heterocyclic compounds that are ligands for nicotinic acetylcholine receptors. The compounds are useful for treating a mammal suffering from any one of a range of therapeutic indications, including Alzheimer's disease, Parkinson's disease, dyskinesias, Tourette's syndrome, schizophrenia, attention deficit disorder, anxiety, pain, depression, obsessive compulsive disorder, chemical substance abuse, alcoholism, memory deficit, pseudodementia, Ganser's syndrome, migraine pain, bulimia, obesity, premenstrual syndrome or late luteal phase syndrome, tobacco abuse, post-traumatic syndrome, social phobia, chronic fatigue syndrome, premature ejaculation, erectile difficulty,
(Continued)

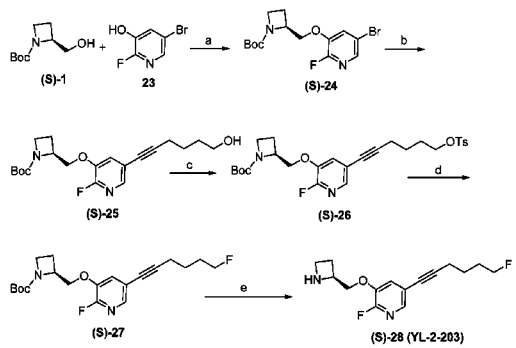

Reagents and conditions: (a) DEAD, PPh₃, THF, 0 °C ~ 40 °C, 12 h, 79%; (b) 5-Hexyn-1-ol, Pd(PPh₃)₂Cl₂ (cat.), CuI (cat.), PPh₃ (cat.), Et₃N/DMSO, 50 °C, overnight, 95%; (c) TsCl, DMAP, Et₃N, DCM, 0 °C ~ r.t., 12 h, 92%; (d) Kryptofix 2.2.2, KF, THF, reflux, overnight, 62%; (e) TFA, CH₂Cl₂, 0 °C ~ r.t., 3 h, 72%.

anorexia nervosa, disorders of sleep, autism, mutism, trichotillomania, and hypothermia.

11 Claims, 2 Drawing Sheets

(58) Field of Classification Search
 USPC ..................................................... 546/268.1
 See application file for complete search history.

(56) References Cited

U.S. PATENT DOCUMENTS

| | | | | |
|---|---|---|---|---|
| 8,642,612 | B2* | 2/2014 | Xiao | ............... A61K 31/4745 514/277 |
| 9,303,017 | B2* | 4/2016 | Xiao | |
| 9,346,784 | B2* | 5/2016 | Brown | ............... C07D 213/65 |
| 2003/0207858 | A1 | 11/2003 | Lee | |
| 2008/0132486 | A1 | 6/2008 | Kozikowski et al. | |
| 2010/0129291 | A1* | 5/2010 | Xiao | ............... A61K 31/4745 424/9.2 |
| 2011/0269733 | A1* | 11/2011 | Brown | ............... C07D 401/12 514/210.2 |
| 2011/0281836 | A1* | 11/2011 | Walker | ............... C07D 401/12 514/210.2 |
| 2014/0323461 | A1* | 10/2014 | Brown | ............... C07D 401/12 514/210.2 |
| 2014/0378428 | A1* | 12/2014 | Xiao | ............... C07D 401/12 514/210.2 |

OTHER PUBLICATIONS

Holladay et al., "Structure-Activity Studies Related to ABT-594, a Potent Nonopioid Analgesic Agent: Effect of Pyridine and Azetidine Ring Substitutions on Nicotinic Acetylcholine Receptor Binding Affinity and Analgesic Activity in Mice," Bioorganic & Medicinal Chemistry Letters, 8:2797-2803 (1998).

Lin et al., "Synthesis and Structure-Activity Relationships of Pyridine-Modified Analogs of 3-[2-((S)-Pyrrolidinyl)Methoxy]pyridine, A-84543, A Poatent Nicotinic Acetylcholine Receptor Agonist," Bioorganic & Medicinal Chemistry Letters, 8:249-254 (1998).

Supplementary European Search Report dated Oct. 10, 2016.

* cited by examiner

Reagents and conditions: (a) DEAD, PPh₃, THF, 0 °C to r.t., 48h, 68–94%; (b) 1-Hexyne or ethynylcyclopropane, Pd(PPh₃)₂Cl₂ (cat.), CuI (cat.), PPh₃ (cat.), Et₃N, DMSO, sealed tube, 95 °C, 60 h (R=CH₃), r.t., overnight ( R=H), 88–98%; (c) Method A: TFA, CH₂Cl₂, 0 °C to r.t., 3 h then 10% NaOH aqueous solution, methanol, 75–83%; Method B: HCl in methanol, 0 °C to r.t., 3 h, 87–92%.

Reagents and conditions: (a) DEAD, PPh$_3$, THF, 0 °C ~ 40 °C, 12 h, 79%; (b) 5-Hexyn-1-ol, Pd(PPh$_3$)$_2$Cl$_2$ (cat.), CuI (cat.), PPh$_3$ (cat.), Et$_3$N/DMSO, 50 °C, overnight, 95%; (c) TsCl, DMAP, Et$_3$N, DCM, 0 °C ~ r.t., 12 h, 92%; (d) Kryptofix 2.2.2, KF, THF, reflux, overnight, 62%; (e) TFA, CH$_2$Cl$_2$, 0 °C ~ r.t., 3 h, 72%.

2-HALO-5-ALKYNYL-PYRIDYL NICOTINIC LIGANDS

RELATED APPLICATIONS

This application is the U.S. national phase of International Patent Application No. PCT/US2014/031873, filed Mar. 26, 2014, which claims benefit of U.S. Provisional Patent Application No. 61/805,646, filed Mar. 27, 2013.

GOVERNMENT SUPPORT

This invention was made with government support under grant numbers U19-DA027990, R21-DA032489, and R03-DA025947 awarded by the National Institutes of Health. The government has certain rights in the invention.

BACKGROUND OF THE INVENTION

Neuronal nicotinic acetylcholine receptors (nAChRs) are ligand-gated cation channels in the central nervous system (CNS) and the peripheral nervous system (PNS). The nAChRs serve a wide range of physiological functions, and have been implicated in a number of pathological processes and pharmacological effects of nicotinic drugs. Many of the important in vivo effects of nicotine in the central nervous system (CNS) are mediated mainly by the desensitization of nAChRs, specifically α4β2 nAChRs, which are the major nAChR subtype in the CNS and the one most clearly affected (up-regulated) by chronic administration of nicotine in rats and mice and by smoking in humans.

The actions of nicotine and other nicotinic agonists to activate and then desensitize nAChRs have been known for more than 100 years and conceptualized for more than 50 years. A fundamental question about nicotinic cholinergic signaling in the CNS and PNS is how each of these two opposite actions contributes to the overall pharmacological effects of nicotinic ligands. It is widely accepted that activation of nAChRs plays important roles in mediating the effects of nicotinic ligands, but many lines of evidence reported in recent years support the notion that the desensitization of nAChRs is also an important mechanism mediating effects of nicotinic drugs. In addition, it is important to note that strong agonist activities of nicotinic drugs on some nAChR subtypes (α3β4 subtype, for example) are responsible for some adverse effects.

Sazetidine-A (Saz-A) is a nAChR ligand which is a selective α4β2 nAChR desensitizer. U.S. Pat. No. 8,030,300 (incorporated by reference). Its major in vitro effect is to desensitize α4β2 nAChRs without affecting either α3β4 or α7 nAChRs. Saz-A shows strong in vivo effects in animal models, including analgesia, reduction in nicotine self-administration, reduction in alcohol intake, antidepressant-like activity, and reversal of attentional impairment. The discovery of novel subtype selective nicotinic ligands that have low efficacy for activation but high potency for desensitization represents an important long-term goal. Effective subtype selective nAChR ligands must also have better chemical and pharmacological properties than those of classical nicotinic ligands and currently marketed nicotinic drugs.

SUMMARY OF THE INVENTION

One aspect of the present invention relates to heterocyclic compounds that are ligands for nicotinic acetylcholine receptors. A second aspect of the invention relates to the use of such a compound for modulation of a mammalian nicotinic acetylcholine receptor. The present invention also relates to the use of such a compound for treating a mammal suffering from Alzheimer's disease, Parkinson's disease, dyskinesias, Tourette's syndrome, schizophrenia, attention deficit disorder, anxiety, pain, depression, obsessive compulsive disorder, chemical substance abuse, alcoholism, memory deficit, pseudodementia, Ganser's syndrome, migraine pain, bulimia, obesity, premenstrual syndrome or late luteal phase syndrome, tobacco abuse, post-traumatic syndrome, social phobia, chronic fatigue syndrome, premature ejaculation, erectile difficulty, anorexia nervosa, disorders of sleep, autism, mutism, or trichtillomania. The present invention also relates to the use of such a compound for treating a mammal suffering from hypothermia.

DETAILED DESCRIPTION OF THE INVENTION

Figure 1:
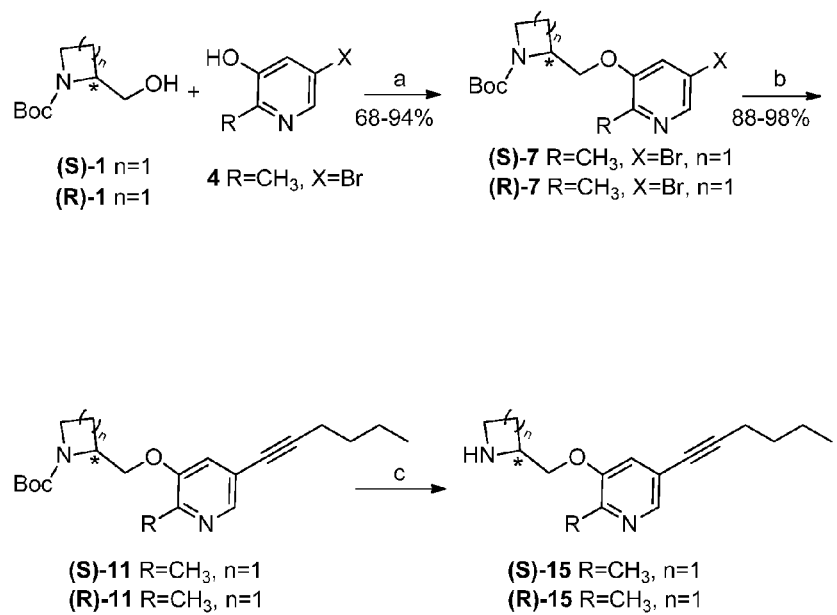
FIG. 1 shows a representative synthesis of compound YL-1-127 and other compounds of the invention.

One aspect of the present invention relates to a compound represented by the formula:

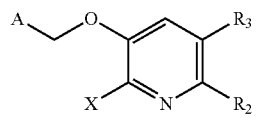

or a pharmaceutically acceptable salt thereof,
wherein, independently for each occurrence,
X is F, Cl, Br, or I;
$R_2$ is H, F, Cl, Br, or I;
$R_3$ is H or substituted or unsubstituted alkyl, alkenyl, alkynyl, alkoxy, cycloalkyl, heterocyclyl, halogen, haloalkyl, hydroxy, cyano, nitro, amino, acyl, aryl, heteroaryl, aroyl, heteroaroyl, aralkyl, heteroaralkyl, aryloxy, heteroaryloxy, carboxy, carboxyalkyl, —$CH_2$—NH—C(O)—$R_6$, —$CH_2$—$CH_2$—C(O)—O-alkyl, or —NH—C(O)-alkyl;
$R_6$ is H, substituted or unsubstituted alkyl, alkoxy, aryl, heteroaryl, aralkyl, heteroaralkyl, or N($R_7$)($R_8$);
$R_7$ is H or substituted or unsubstituted alkyl;
$R_8$ is H, substituted or unsubstituted alkyl, or aryl; and
A is selected from the group consisting of

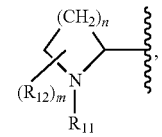
(a)

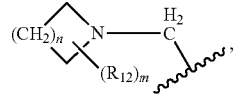
(b)

-continued (c)
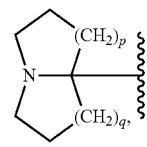

(d)
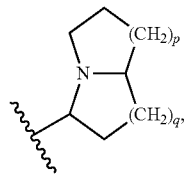

(e)
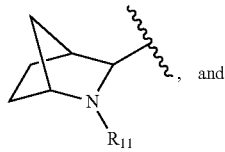

(f)
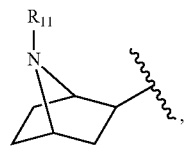

wherein,
m is 0, 1, 2, 3, 4, or 5;
n is 1, 2, or 3;
p and q are independently 1 or 2;
$R_{11}$ is H, alkyl, or alkenyl;
$R_{12}$ is alkyl, alkoxy, alkoxyalkyl, cyano, halogen, hydroxy, hydroxyalkyl, haloalkyl, —O—C(O)-alkyl, or —O-methanesulfonyl;
wherein, if present, each substituent is independently alkyl, alkenyl, alkynyl, alkoxy, amino, aryl, aralkyl, heteroaralkyl, heteroaryl, cyano, nitro, haloalkyl, cycloalkyl, heterocyclyl, halogen, or hydroxy; and
wherein the absolute stereochemistry at a stereogenic center may be R or S or a mixture thereof; and the stereochemistry of a double bond may be E or Z or a mixture thereof.

In certain embodiments, X is F or Cl.
In other embodiments, X is Cl.
In yet other embodiments, X is F.
In certain embodiments, $R_2$ is H.
In other embodiments, $R_2$ is F or Cl.
In other embodiments, $R_2$ is F.
In certain embodiments, $R_2$ is Cl.
In certain embodiments, $R_3$ is substituted or unsubstituted alkyl, alkenyl, or alkynyl.
In certain other embodiments, $R_3$ is substituted or unsubstituted alkoxy or haloalkyl.
In certain embodiments, $R_3$ is substituted or unsubstituted aryl, heteroaryl, aralkyl, or heteroaralkyl.
In certain other embodiments, $R_3$ is substituted or unsubstituted aroyl, heteroaroyl, aryloxy, or heteroaryloxy.
In certain embodiments, $R_3$ is halogen.
In other embodiments, $R_3$ is Br, Cl, or F.
In another embodiment, $R_3$ is —N($R_4$)($R_5$), wherein $R_4$ and $R_5$ are independently hydrogen, substituted or unsubstituted alkyl, aryl, heteroaryl, aralkyl, or heteroaralkyl.

In another embodiment, $R_3$ is

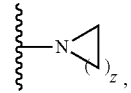

wherein z is 1, 2, 3, or 4.
In yet another embodiment, $R_3$ is —C(O)—$R_6$, where $R_6$ is H, substituted or unsubstituted alkyl, alkoxy, aryl, heteroaryl, aralkyl, heteroaralkyl, or N($R_7$)($R_8$), wherein $R_7$ is H or substituted or unsubstituted alkyl; and $R_8$ is H, substituted or unsubstituted alkyl, or aryl.
In certain other embodiments, $R_3$ is —O$R_9$, wherein $R_9$ is alkyl, aryl, heteroaryl, aralkyl, heteroaralkyl or —CON($R_4$)($R_5$), wherein $R_4$ and $R_5$ are independently hydrogen, substituted or unsubstituted alkyl, aryl, heteroaryl, or aralkyl.
In another embodiment, $R_3$ is substituted or unsubstituted benzyl, phenyl, naphthyl, or biphenyl.
In yet another embodiment, $R_3$ is substituted or unsubstituted alkyl.
In other embodiments, $R_3$ is substituted or unsubstituted alkenyl.
In another embodiment, $R_3$ is substituted or unsubstituted alkynyl.
In other embodiments, $R_3$ is

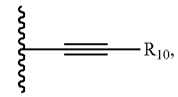

wherein $R_{10}$ is selected from the group consisting of H, hydroxy, halogen, and substituted and unsubstituted alkyl, cycloalkyl, aryl, aralkyl, heteroaryl, and heteroaralkyl; wherein each substituent is independently selected from the group consisting of alkyl, alkenyl, alkynyl, alkoxy, amino, aryl, aralkyl, heteroaralkyl, heteroaryl, cyano, nitro, haloalkyl, cycloalkyl, heterocyclyl, halogen, and hydroxy.

In certain other embodiments, $R_3$ is selected from the group consisting of

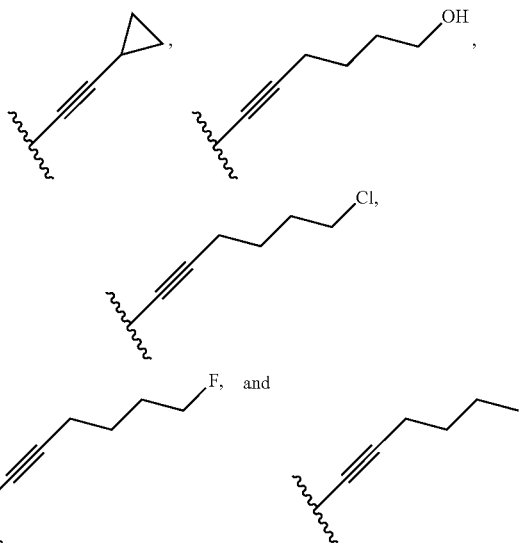

In certain embodiments, A is

[structure: azetidine-type ring with (CH₂)ₙ, (R₁₂)ₘ, N–R₁₁]

In other embodiments, A is

[structure: (CH₂)ₙ–N–CH₂– with (R₁₂)ₘ]

In another embodiment, A is

[structure: pyrrolidine-type spiro with (CH₂)ₚ and (CH₂)_q]

In yet another embodiment, A is

[structure: bicyclic N-containing with (CH₂)ₚ and (CH₂)_q]

In another embodiment, A is

[structure: bicyclic azabicycle with N–R₁₁]

In another embodiment, A is

[structure: bicyclic azabicycle with R₁₁ on N]

In certain embodiments, R₁₁ is H; and m is 0.
In other embodiments, n is 1.
In certain other embodiments, n is 2.
In certain embodiments, R₁₁ is H; m is 0; and n is 1. In other embodiments, R₁₁ is H;
m is 0; and n is 2.
In another embodiment, X is F or Cl; R₂ is H; R₃ is substituted or unsubstituted alkynyl; and A is

[structure: azetidine ring with (CH₂)ₙ, (R₁₂)ₘ, N–R₁₁]

In yet another embodiment, X is F; R₂ is H; R₃ is

[structure: –C≡C–R₁₀]

wherein R₁₀ is selected from the group consisting of H, hydroxy, halogen, and substituted and unsubstituted alkyl, cycloalkyl, aryl, aralkyl, heteroaryl, and heteroaralkyl; wherein each substituent is independently selected from the group consisting of alkyl, alkenyl, alkynyl, alkoxy, amino, aryl, aralkyl, heteroaralkyl, heteroaryl, cyano, nitro, haloalkyl, cycloalkyl, heterocyclyl, halogen, and hydroxy; and A is

[structure: azetidine ring with (CH₂)ₙ, (R₁₂)ₘ, N–R₁₁]

In certain embodiments, X is F; R₂ is H; R₃ is selected from the group consisting of

[structures: –C≡C–cyclopropyl, –C≡C–(CH₂)₄–OH, –C≡C–(CH₂)₅–Cl, –C≡C–(CH₂)₄–F, and –C≡C–(CH₂)₄–CH₃]

and A is

[structure: azetidine ring with (CH₂)ₙ, (R₁₂)ₘ, N–R₁₁]

In another embodiment, $R_{11}$ is H; m is 0; and n is 1. In yet another embodiment, $R_{11}$ is H; m is 0; and n is 2.

In certain embodiments, the compound has the structure:

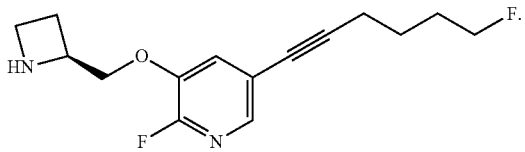 [SMILES: FCCCCC#Cc1cnc(F)c(OC[C@@H]2CCN2)c1]

In another embodiment, the compound has an $IC_{50}$ less than 1 µM (micromolar) in an assay based on a mammalian nicotinic ACh receptor.

In another embodiment, the compound has an $IC_{50}$ less than 100 nM (nanomolar) in an assay based on a mammalian nicotinic ACh receptor.

In yet another embodiment, the compound has an $IC_{50}$ less than 10 nM in an assay based on a mammalian nicotinic ACh receptor.

In another embodiment, the compound has an $IC_{50}$ less than 1 nM in an assay based on a mammalian nicotinic ACh receptor.

In one embodiment, the compound has an $EC_{50}$ less than 1 µM in an assay based on a mammalian nicotinic ACh receptor.

In another embodiment, the compound has an $EC_{50}$ less than 100 nM in an assay based on a mammalian nicotinic ACh receptor.

In yet another embodiment, the compound has an $EC_{50}$ less than 10 nM in an assay based on a mammalian nicotinic ACh receptor.

In yet another embodiment, the compound has an $EC_{50}$ less than 1 nM in an assay based on a mammalian nicotinic ACh receptor.

In certain embodiments, the compound is a single stereoisomer.

Another aspect of the present invention relates to a pharmaceutical composition, comprising any one of the aforementioned compounds; and a pharmaceutically acceptable excipient.

In certain embodiments, the pharmaceutical composition is formulated as an oral dosage form. In certain embodiments, the oral dosage form is a tablet, pill, or capsule.

Yet another aspect of the present invention relates to method of modulating a nicotinic ACh receptor, comprising administering to a mammal in need thereof an effective amount of any one of the aforementioned compounds.

In certain embodiments, the mammal is a primate, equine, canine, or feline. In certain embodiments, the mammal is a human.

In certain embodiments, the compound is administered orally. In other embodiments, the compound is administered intravenously. In another embodiment, the compound is administered sublingually. In yet another embodiment, the compound is administered ocularly. In another embodiment, the compound is administered transdermally. In yet another embodiment, the compound is administered rectally. In another embodiment, the compound is administered vaginally. In another embodiment, the compound is administered topically. In yet another embodiment, the compound is administered intramuscularly. In another embodiment, the compound is administered subcutaneously. In certain embodiments, the compound is administered buccally. In certain other embodiments, the compound is administered nasally.

Another aspect of the present invention relates to a method of treating Alzheimer's disease, Parkinson's disease, dyskinesias, Tourette's syndrome, schizophrenia, attention deficit disorder, anxiety, pain, depression, obsessive compulsive disorder, chemical substance abuse, alcoholism, memory deficit, pseudodementia, Ganser's syndrome, migraine pain, bulimia, obesity, premenstrual syndrome or late luteal phase syndrome, tobacco abuse, post-traumatic syndrome, social phobia, chronic fatigue syndrome, premature ejaculation, erectile difficulty, anorexia nervosa, disorders of sleep, autism, mutism, or trichotillomania. The method comprises administering to a mammal in need thereof a therapeutically effective amount of any one of the aforementioned compounds.

In certain embodiments, the mammal is a primate, equine, canine, or feline. In certain embodiments, the mammal is a human.

In certain embodiments, the compound is administered orally. In other embodiments, the compound is administered intravenously. In another embodiment, the compound is administered sublingually. In yet another embodiment, the compound is administered ocularly. In another embodiment, the compound is administered transdermally. In yet another embodiment, the compound is administered rectally. In another embodiment, the compound is administered vaginally. In another embodiment, the compound is administered topically. In yet another embodiment, the compound is administered intramuscularly. In another embodiment, the compound is administered subcutaneously. In certain embodiments, the compound is administered buccally. In certain other embodiments, the compound is administered nasally.

Another aspect of the present invention relates to a method of treating hypothermia. The method comprises administering to a mammal in need thereof a therapeutically effective amount of any one of the aforementioned compounds.

In certain embodiments, the mammal is a primate, equine, canine, or feline. In certain embodiments, the mammal is a human.

In certain embodiments, the compound is administered orally. In other embodiments, the compound is administered intravenously. In another embodiment, the compound is administered sublingually. In yet another embodiment, the compound is administered ocularly. In another embodiment, the compound is administered transdermally. In yet another embodiment, the compound is administered rectally. In another embodiment, the compound is administered vaginally. In another embodiment, the compound is administered topically. In yet another embodiment, the compound is administered intramuscularly. In another embodiment, the compound is administered subcutaneously. In certain embodiments, the compound is administered buccally. In certain other embodiments, the compound is administered nasally.

Definitions

For convenience, certain terms employed in the specification, examples, and appended claims are collected here.

The articles "a" and "an" are used herein to refer to one or to more than one (i.e., to at least one) of the grammatical object of the article. By way of example, "an element" means one element or more than one element.

The term "$ED_{50}$" means the dose of a drug which produces 50% of its maximum response or effect. Alternatively, "ED$_{50}$" means the dose which produces a pre-determined response in 50% of test subjects or preparations.

The term "LD$_{50}$" means the dose of a drug which is lethal in 50% of test subjects.

The term "therapeutic index" refers to the therapeutic index of a drug defined as LD$_{50}$/ED$_{50}$.

The term "structure-activity relationship (SAR)" refers to the way in which altering the molecular structure of drugs alters their interaction with a receptor, enzyme, etc.

The term "agonist" refers to a compound that mimics the action of natural transmitter or, when the natural transmitter is not known, causes changes at the receptor complex in the absence of other receptor ligands.

The term "antagonist" refers to a compound that binds to a receptor site, but does not cause any physiological changes unless another receptor ligand is present.

The term "inverse agonist" refers to a compound that binds to a constitutively active receptor site and reduces its physiological function.

The term "competitive antagonist" refers to a compound that binds to a receptor site; its effects can be overcome by increased concentration of the agonist.

The term "partial agonist" refers to a compound that binds to a receptor site but does not produce the maximal effect regardless of its concentration.

The term "ligand" refers to a compound that binds at the receptor site.

The term "heteroatom" as used herein means an atom of any element other than carbon or hydrogen. Preferred heteroatoms are boron, nitrogen, oxygen, phosphorus, sulfur and selenium.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., C$_1$-C$_{30}$ for straight chain, C$_3$-C$_{30}$ for branched chain), and more preferably 20 or fewer. Likewise, preferred cycloalkyls have from 3-10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond, respectively.

The term "aryl" as used herein includes 5-, 6-, and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta, and para apply to 1,2-, 1,3-, and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, azetidine, azepine, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle", as used herein, refers to an aromatic or non-aromatic ring in which each atom of the ring is carbon.

As used herein, the term "nitro" means —NO$_2$; the term "halogen" designates —F, —Cl, —Br, or —I; the term "sulfhydryl" means —SH; the term "hydroxyl" means —OH; and the term "sulfonyl" means —SO$_2$—.

The terms "amine" and "amino" are art-recognized and refer to both unsubstituted and substituted amines, e.g., a moiety that can be represented by the general formula:

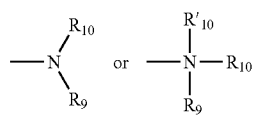

wherein $R_9$, $R_{10}$, and $R'_{10}$ each independently represent a group permitted by the rules of valence.

The term "acylamino" is art-recognized and refers to a moiety that can be represented by the general formula:

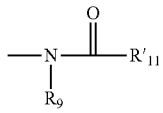

wherein $R_9$ is as defined above, and $R'_{11}$ represents a hydrogen, an alkyl, an alkenyl or $-(CH_2)_m-R_8$, where m and $R_8$ are as defined above.

The term "amido" is art-recognized as an amino-substituted carbonyl and includes a moiety that can be represented by the general formula:

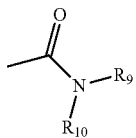

wherein $R_9$ and $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m-R_8$, wherein m and $R_8$ are defined above. Representative alkylthio groups include methylthio, ethyl thio, and the like.

The term "carbonyl" is art-recognized and includes such moieties as can be represented by the general formula:

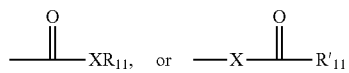

wherein X is a bond or represents an oxygen or a sulfur, and $R_{11}$ represents a hydrogen, an alkyl, an alkenyl, $-(CH_2)_m-R_8$ or a pharmaceutically acceptable salt, $R'_{11}$ represents a hydrogen, an alkyl, an alkenyl or $-(CH_2)_m-R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester". Where X is a sulfur and $R_{11}$ is hydrogen, the formula represents a "thiolcarboxylic acid". Where X is a sulfur and $R'_{11}$ is hydrogen, the formula represents a "thiolformate". On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O— alkenyl, —O-alkynyl, —O—$(CH_2)_m-R_8$, where m and $R_8$ are described above.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations. The abbreviations contained in said list, and all abbreviations utilized by organic chemists of ordinary skill in the art are hereby incorporated by reference.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g., alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991).

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, it may be isolated using chiral chromatography methods, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., functioning as analgesics), wherein one or more simple variations of substituents are made which do not adversely affect the efficacy of the compound in binding to opioid receptors. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, *Handbook of Chemistry and Physics,* 67th Ed., 1986-87, inside cover.

Dosages

The dosage of any compositions of the present invention will vary depending on the symptoms, age and body weight of the patient, the nature and severity of the disorder to be treated or prevented, the route of administration, and the form of the subject composition. Any of the subject formulations may be administered in a single dose or in divided doses. Dosages for the compositions of the present invention may be readily determined by techniques known to those of skill in the art or as taught herein.

In certain embodiments, the dosage of the subject compounds will generally be in the range of about 0.01 ng to about 10 g per kg body weight, specifically in the range of about 1 ng to about 0.1 g per kg, and more specifically in the range of about 100 ng to about 10 mg per kg.

An effective dose or amount, and any possible effects on the timing of administration of the formulation, may need to be identified for any particular composition of the present invention. This may be accomplished by routine experiment as described herein, using one or more groups of animals (preferably at least 5 animals per group), or in human trials if appropriate. The effectiveness of any subject composition and method of treatment or prevention may be assessed by administering the composition and assessing the effect of the administration by measuring one or more applicable indices, and comparing the post-treatment values of these indices to the values of the same indices prior to treatment.

The precise time of administration and amount of any particular subject composition that will yield the most effective treatment in a given patient will depend upon the activity, pharmacokinetics, and bioavailability of a subject composition, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the patient may be monitored by measuring one or more of the relevant indices at predetermined times during the treatment period. Treatment, including composition, amounts, times of administration and formulation, may be optimized according to the results of such monitoring. The patient may be periodically reevaluated to determine the extent of improvement by measuring the same parameters. Adjustments to the amount(s) of subject composition administered and possibly to the time of administration may be made based on these reevaluations.

Treatment may be initiated with smaller dosages which are less than the optimum dose of the compound. Thereafter, the dosage may be increased by small increments until the optimum therapeutic effect is attained.

The use of the subject compositions may reduce the required dosage for any individual agent contained in the compositions because the onset and duration of effect of the different agents may be complimentary.

Toxicity and therapeutic efficacy of subject compositions may be determined by standard pharmaceutical procedures in cell cultures or experimental animals, e.g., for determining the $LD_{50}$ and the $ED_{50}$.

The data obtained from the cell culture assays and animal studies may be used in formulating a range of dosage for use in humans. The dosage of any subject composition lies preferably within a range of circulating concentrations that include the $ED_{50}$ with little or no toxicity. The dosage may vary within this range depending upon the dosage form employed and the route of administration utilized. For compositions of the present invention, the therapeutically effective dose may be estimated initially from cell culture assays.

Formulation

The compositions of the present invention may be administered by various means, depending on their intended use, as is well known in the art. For example, if compositions of the present invention are to be administered orally, they may be formulated as tablets, capsules, granules, powders or syrups. Alternatively, formulations of the present invention may be administered parenterally as injections (intravenous, intramuscular or subcutaneous), drop infusion preparations or suppositories. For application by the ophthalmic mucous membrane route, compositions of the present invention may be formulated as eye drops or eye ointments. These formulations may be prepared by conventional means, and, if desired, the compositions may be mixed with any conventional additive, such as an excipient, a binder, a disintegrating agent, a lubricant, a corrigent, a solubilizing agent, a suspension aid, an emulsifying agent or a coating agent.

In formulations of the subject invention, wetting agents, emulsifiers and lubricants, such as sodium lauryl sulfate and magnesium stearate, as well as coloring agents, release agents, coating agents, sweetening, flavoring and perfuming agents, preservatives and antioxidants may be present in the formulated agents.

Subject compositions may be suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of composition that may be combined with a carrier material to produce a single dose vary depending upon the subject being treated, and the particular mode of administration.

Methods of preparing these formulations include the step of bringing into association compositions of the present invention with the carrier and, optionally, one or more accessory ingredients. In general, the formulations are prepared by uniformly and intimately bringing into association agents with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and *acacia* or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and *acacia*), each containing a predetermined amount of a subject composition thereof as an active ingredient. Compositions of the present invention may also be administered as a bolus, electuary, or paste.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or *acacia*; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent. Formulations which are suitable for vaginal administration also include pessaries, tampons, creams, gels, pastes, foams or spray formulations containing such carriers as are known in the art to be appropriate.

Dosage forms for transdermal administration of a subject composition includes powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions of the present invention may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions.

Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of this invention suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

Kits

This invention also provides kits for conveniently and effectively implementing the methods of this invention. Such kits comprise any subject composition, and a means for facilitating compliance with methods of this invention. Such kits provide a convenient and effective means for assuring that the subject to be treated takes the appropriate active in the correct dosage in the correct manner. The compliance means of such kits includes any means which facilitates administering the actives according to a method of this invention. Such compliance means include instructions, packaging, and dispensing means, and combinations thereof. Kit components may be packaged for either manual or partially or wholly automated practice of the foregoing methods. In other embodiments involving kits, this invention contemplates a kit including compositions of the present invention, and optionally instructions for their use.

EXEMPLIFICATION

The invention now being generally described, it will be more readily understood by reference to the following examples which are included merely for purposes of illustration of certain aspects and embodiments of the present invention, and are not intended to limit the invention.

Example 1

Pharmacological Properties

We measured the in vitro binding affinities of the ligands for defined receptor subtypes ($\alpha2\beta2$, $\alpha2\beta4$, $\alpha3\beta2$, $\alpha3\beta4$, $\alpha4\beta2$, $\alpha4\beta4$, $\alpha6\beta2$, $\alpha6\beta4$, and $\alpha7$) expressed in stably transfected cell lines. [$^3$H]Epibatidine ([$^3$H]EB) binds to the agonist recognition site of all of the defined receptor subtypes with high affinities. Rat forebrain homogenates were included to allow comparison between the heterologous and native $\alpha4\beta2$ and $\alpha7$ nAChRs. See Table 1 for binding affinity values ($K_i$) of the ligands at the three major nAChR subtypes ($\alpha3\beta4$, $\alpha4\beta2$ and $\alpha7$).

Compounds YL-1-127 and YL-2-203 are hereafter abbreviated (S)-15 and (S)-28, respectively. The compound (S)-15 represents an important benchmark compound we recently prepared, while (S)-28 is among the various compounds constituting the present invention. The presence of a halogen in the 2-position of the pyridine ring, such as in (S)-28, was unexpectedly discovered greatly to improve the desired binding activity and selectivity, as well as the pharmacological properties. Preliminary studies of (S)-15 and (S)-28 in animal models indicate that these ligands may have a better adverse effect profile than those of other nicotinic ligands.

TABLE 1

In Vitro Pharmacological Properties of Nicotinic Ligands

| Compound | $K_i$ (nM) | | |
|---|---|---|---|
| | $\alpha3\beta4$ | $\alpha4\beta2$ | $\alpha7$ |
| (−)-Nicotine | 180 | 14 | 517 |
| Varenicline | 27 | 0.14 | 37 |
| Sazetidine-A | 6.5 | 0.034 | 670 |
| YL-1-127 | 575 | 14 | 93,000 |
| YL-2-203 | 93 | 0.2 | 11,000 |

Example 2

In Vitro Binding Affinities for nAChR Subtypes

The binding affinities of the novel 2-halo-5-substituted pyridinyl analogs for the defined rat nAChR subtypes as well as for native nAChRs of rat forebrain were examined in binding competition studies against [$^3$H]-epibatidine. For comparison, binding affinities of (−)-nicotine, varenicline and Sazetidine-A were obtained from parallel binding experiments. To determine selectivities of these compounds in binding assays among the three predominant nAChR subtypes, $\alpha3\beta4$, $\alpha4\beta2$, and $\alpha7$, the ratios of $K_i$ values ($\alpha3\beta4/\alpha4\beta2$ and $\alpha7/\alpha4\beta2$) were determined.

The functional properties of the ligands were determined by $^{86}$Rb$^+$ efflux assays in cells expressing $\alpha3\beta4$ and $\alpha4\beta2$ nAChR subtypes. The functional activity of each ligand was measured for its agonism, antagonism and desensitization ability. Agonist activity for each of the ligands was tested at eight different concentrations. The responses were compared to that stimulated by 100 µM (−)-nicotine, a near maximally effective concentration. The full concentration-effect curves generated potency (EC$_{50}$) and efficacy (E$_{max}$) of each ligand. The antagonist activity of each ligand was determined by applying the ligand to cells simultaneously with 100 µM (−)-nicotine. Each ligand was tested for antagonist activity at eight concentrations. The potency (IC$_{50(0')}$) of each ligand as an antagonist was derived from the full concentration-effect curves. The desensitization potency of each ligand was determined by pre-treating cells with the test compound for 10 minutes before 100 µM (−)-nicotine was applied. The potency of a ligand to desensitize the receptor after a 10 minute exposure (IC$_{50(10')}$) was obtained with full concentration-effect curves using at least 8 concentrations of the ligand. Although $^{86}$Rb$^+$ efflux assays are mainly used to determine functional properties, whole cell current measurements were also used to verify the key experiments. See Table 1 below for potency of the compounds to desensitize the two major receptor (IC$_{50(10')}$) subtypes, $\alpha3\beta4$ and $\alpha4\beta2$. ND indicates no significant stimulated efflux was detected.

In Vitro Effects on nAChR Function.

New compounds showing high binding affinities for $\alpha4\beta2$ nAChRs and high selectivities for this subtype over $\alpha3\beta4$ and $\alpha7$ receptors in binding assays were chosen for functional studies (Table 2). Their agonist activities were assessed by measuring stimulated $^{86}Rb^+$ efflux from stably transfected cells, either expressing human α4β2 nAChRs or rat α3β4 receptors. Their abilities to desensitize the two nAChR subtypes were determined by measuring nicotine-stimulated $^{86}Rb^+$ efflux after cells were pre-incubated with the test compounds for 10 min. For comparison, nicotine, varenicline, and Sazetidine-A were included in the experiments.

As expected, nicotine showed full agonist activities at both human α4β2 and rat α3β4 nAChRs (Table 2). Consistent with previous reports, compared to those of (−)-nicotine, varenicline had 45% of efficacy in stimulating efflux from cells expressing the α4β2 nAChRs and 90% of efficacy from cells expressing the α3β4 nAChRs. Sazetidine-A showed slightly lower efficacy at the α4β2 nAChRs than that of varenicline. In contrast, Sazetidine-A's agonist activity at the α3β4 nAChRs was much lower than that of (−)-nicotine and varenicline. Consistent with the purposes of developing this line of novel ligands, all compounds tested show much lower agonist activities than those of Sazetidine-A at both receptor subtypes. (S)-15 and (S)-28 had less than 33% agonist efficacy at the α4β2 nAChRs. (S)-15 and (S)-28 did not show detectable agonist activity at the receptor subtype. In fact, all compounds showed no detectable agonist activity at the α3β4 nAChRs.

As expected, (−)-nicotine, varenicline and Sazetidine-A potently and selectively desensitize α4β2 nAChRs with $IC_{50(10')}$ values in nM range (Table 2). (S)-15 and (S)-28 maintained the ability to selectively desensitize the α4β2 nAChRs. Their $IC_{50(10')}$ values for desensitizing α4β2 nAChRs were 260 nM for (S)-15 and 35 nM for (S)-28, an unexpectedly large improvement considering their structural similarity. Their $IC_{50(10')}$ values for desensitizing α3β4 nAChRs were 9,200 nM and 6,000 nM. Importantly, compound (S)-28 displayed a dramatic improvement in agonist efficacy ($E_{max}$) at the α3β4 receptor as compared with Sazetidine-A. While Sazetidine-A displayed an $E_{max}$ of 96%, (S)-28 resulted in only 26% efficacy.

TABLE 2

Comparison of Activation and Desensitization of nAChR Function by Ligands

| Compound | α3β4 | | | α4β2 | | |
|---|---|---|---|---|---|---|
| | $EC_{50}$ (nM) | $E_{max}$ (%) | $IC_{50(10')}$ (nM) | $EC_{50}$ (nM) | $E_{max}$ (%) | $IC_{50(10')}$ (nM) |
| (−)-Nicotine | 18,000 | 100 | 16,000 | 2,400 | 100 | 370 |
| Varenicline | 3,200 | 82 | 4,300 | 950 | 45 | 94 |
| Sazetidine-A | 730 | 96 | 1,300 | 24 | 40 | 11 |
| YL-1-127 | 11,000 | 10 | 9,200 | 310 | 15 | 260 |
| YL-2-203 | 6,300 | 26 | 6,000 | 35 | 33 | 35 |

Example 3

Design and Synthesis of Compounds

The compounds of the invention may be prepared by any conventional method useful for the preparation of analogous compounds and as described in the examples below.

Starting materials for the processes described in the present patent application are known or can be prepared by known processes from commercially available materials.

A compound of the invention can be converted to another compound of the invention using conventional methods.

The products of the reactions described herein are isolated by conventional means such as extraction, crystallization, distillation, chromatography, and the like.

Figure 2:
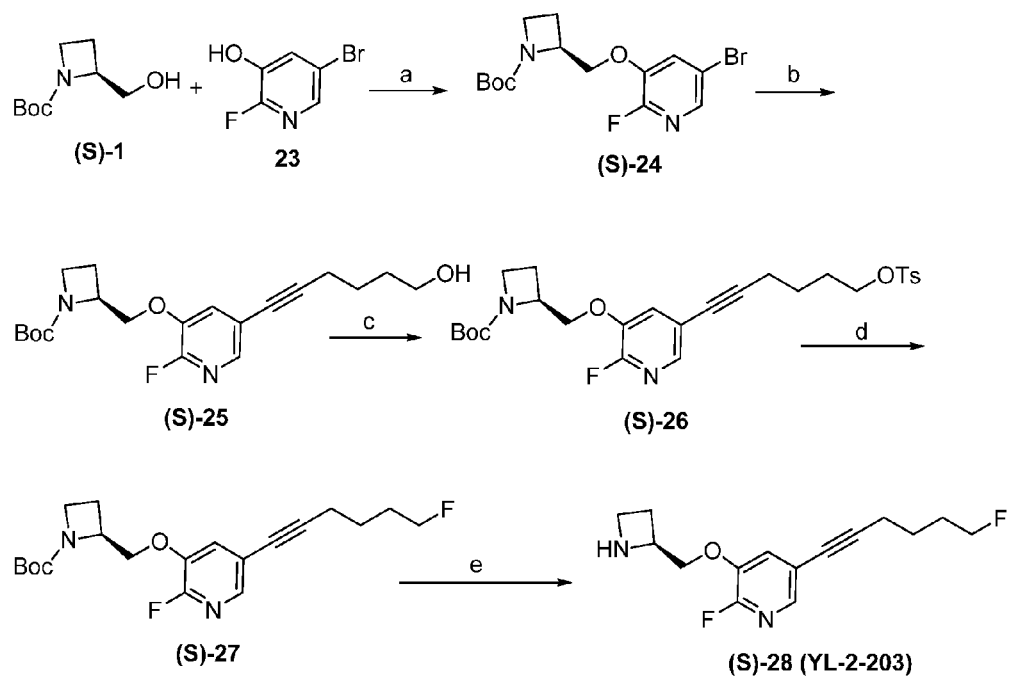
FIG. 2 shows a representative synthesis of compound YL-2-203 and other compounds of the invention.

Examples of the nicotinic ACh receptor ligands of the present invention may be prepared by the general methods described hereinafter. The general sequence of chemical reactions used to prepare the compounds described herein is shown in FIGS. 1 and 2.

General Chemistry Methods.

All solvents and reagents were used as obtained from commercial sources unless otherwise indicated. All starting materials were also obtained from commercial source. All reactions were performed under nitrogen atmosphere unless otherwise noted. Organic phases were washed with water, brine, dried over anhydrous $Na_2SO_4$ and evaporated at 40° C. under reduced pressure (standard work up). $^1H$ and $^{13}C$ NMR spectra were recorded on a Varian-400 spectrometer operating at 400 MHz for $^1H$ and 100 MHz for $^{13}C$. Deuterated chloroform (99.8% D) was used as solvents. $^1H$ Chemical shifts value (δ), from tetramethylsilane as internal standard. $^{13}C$ chemical shifts (δ) are referenced to $CDCl_3$ (central peak, δ=77.00 ppm) as the internal standard. Optical rotation was detected on ADP220 Automatic polarimeter from Bellingham & Stanley Limited. Mass spectra were measured in positive mode electrospray ionization (ESI). The HRMS data were obtained on a Waters Q-TOF Premier mass spectrometer. TLC was performed on silica gel 60 $F_{254}$ plastic sheets. Column chromatography was performed using silica gel (35-75 mesh). Combustion analyses were performed by Atlantic Microlabs, Inc. Norcross, Ga.

General Procedure for the Mitsunobu Reaction.

To a mixture of the N-Boc protected alcohol (1.0 equiv), the 5-halogen-3-pyridinol (1.0 equiv), and $Ph_3P$ (1.3 equiv) in anhydrous THF (0.1 M) was added DEAD (1.3 equiv) dropwise at 0° C. under nitrogen atmosphere. After stirring for 2 days at room temperature, the solvent was removed under reduced pressure. The residue was purified by column chromatography on silica gel using a gradient of hexane-ethyl acetate (10:1 to 5:1) as the eluent to give the product in 68%-90% yield.

General Procedure (Method A) for the Sonogashira Coupling Reaction.

A mixture of the Mitsunobu adduct (1 equiv), alkyne (4 equiv), $Pd(PPh_3)_2Cl_2$ (0.05 equiv), CuI (0.1 equiv), $PPh_3$ (0.1 equiv) in $Et_3N$/DMSO (10:1, 0.12 M) was stirred overnight at room temperature under a nitrogen atmosphere. The reaction mixture was taken up in ethyl acetate, and the organic phase was washed with water, brine, and then dried over $Na_2SO_4$. The extract was concentrated under reduced pressure, and the residue was purified by column chromatography on silica gel using a gradient of $CH_2Cl_2$-ethyl acetate (16:1 to 10:1) as the eluent to give the product in 88-98% yield.

General Procedure (Method B) for the Sonogashira Coupling Reaction.

A mixture of the Mitsunobu adduct (1 equiv), alkyne (4 equiv), $Pd(PPh_3)_2Cl_2$ (0.05 equiv), CuI (0.1 equiv), $PPh_3$ (0.1 equiv) in $Et_3N$/DMSO (10:1, 0.12 M) was heated to 95° C. under a nitrogen atmosphere in a sealed tube for 60 h. The cooled reaction mixture was taken up in ethyl acetate, and the organic phase was washed with water, brine, and then dried over $Na_2SO_4$. The extract was concentrated under a reduced pressure, and the residue was purified by column chromatography on silica gel using a gradient of $CH_2Cl_2$-ethyl acetate (16:1 to 10:1) as the eluent to give the product in 88-98% yield.

General Procedure (Method C) for Deprotection of the N-Boc Group.

To a stirred solution of the Sonogashira adduct (1 equiv) in dichloromethane (0.1 M) was added trifluoroacetic acid (32 equiv) dropwise at 0° C. under a nitrogen atmosphere. The reaction mixture was stirred for 3 h at room temperature. The solvent and excess TFA was then removed under reduced pressure. To the residue was added 2-3 mL of methanol was added followed by dropwise addition of 10% aqueous NaOH solution at 0° C. until the pH of the mixture was 9-10. After the mixture was stirred at room temperature for 30 min, the solution was taken up in dichloromethane, and the organic phase was washed with brine, dried over $Na_2SO_4$. The extract was concentrated under reduced pressure. The residue was purified by column chromatography on silica gel using a gradient of $CH_2Cl_2$-methanol (20:1 to 10:1) as the eluent to give the product in 75-83% yield.

General Procedure (Method D) for Deprotection of the N-Boc Group.

To Boc protected compound (1 mmol), the solution of 2 M HCl in Methanol (10 mL) was added at 0° C. under a nitrogen atmosphere. The reaction mixture was allowed to warm to room temperature and stirred for 3 hours. The reaction mixture was concentrated under a reduced pressure, and the residue was purified by column chromatography on silica gel using a gradient of $CH_2Cl_2$-Methanol (10:1 to 5:1) as the eluent to give the product as white solid in 73-92% yield.

(S)-tert-butyl-2-((5-Bromo-2-methylpyridin-3-yloxy)methyl)azetidine-1-carboxylate ((S)-7)

Yield: 69% (light red solid). $^1$H NMR (CDCl$_3$, 400 MHz): δ 8.15 (s, 1H), 7.26 (s, 1H), 4.52 (m, 1H), 4.33 (m, 1H), 4.05 (m, 1H), 3.90 (m, 2H), 2.45 (s, 3H), 2.34 (m, 2H), 1.41 (s, 9H).

(R)-tert-butyl-2-((5-bromo-2-methylpyridin-3-yloxy)methyl)azetidine-1-carboxylate ((R)-7)

Yield: 77% (light red solid). $^1$H NMR (CDCl$_3$, 400 MHz): δ 8.16 (s, 1H), 7.26 (s, 1H), 4.53 (m, 1H), 4.34 (m, 1H), 4.06 (m, 1H), 3.91 (m, 2H), 2.45 (s, 3H), 2.35 (m, 2H), 1.42 (s, 9H).

(S)-tert-butyl-2-((5-(hex-1-ynyl)-2-methylpyridin-3-yloxy)methyl)azetidine-1-carboxylate ((S)-11)

Method B was used. Yield: 95% (light yellow oil). $^1$H NMR (CDCl$_3$, 400 MHz): δ 8.12 (d, 1H, J=1.2 Hz), 7.10 (d, 1H, J=1.2 Hz), 4.52 (m, 1H), 4.32 (m, 1H), 4.05 (dd, 1H, J=10, 2.8 Hz), 3.90 (m, 2H), 2.48 (s, 3H), 2.41 (t, 2H, J=7.2 Hz), 2.33 (m, 2H), 1.59 (m, 2H), 1.48 (m, 2H), 1.41 (s, 9H), 0.95 (t, 3H, J=7.2 Hz).

(R)-tert-butyl-2-((5-(hex-1-ynyl)-2-methylpyridin-3-yloxy)methyl)azetidine-1-carboxylate ((R)-11)

Method B was used. Yield: 93% (light yellow oil). $^1$H NMR (CDCl$_3$, 400 MHz): δ 8.10 (d, 1H, J=1.2 Hz), 7.09 (d, 1H, J=1.2 Hz), 4.50 (m, 1H), 4.30 (m, 1H), 4.03 (dd, 1H, J=10, 2.8 Hz), 3.89 (m, 2H), 2.46 (s, 3H), 2.39 (t, 2H, J=7.2 Hz), 2.31 (m, 2H), 1.57 (m, 2H), 1.46 (m, 2H), 1.39 (s, 9H), 0.94 (t, 3H, J=7.2 Hz).

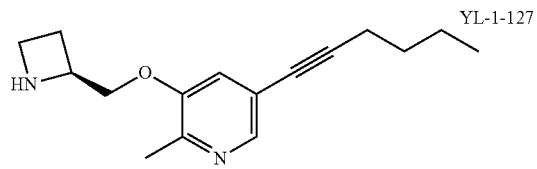 [SMILES: CCCCC#Cc1cnc(C)c(OC[C@@H]2CCN2)c1]

(S)-3-(azetidin-2-ylmethoxy)-5-(hex-1-ynyl)-2-methylpyridine ((S)-15) (YL-1-127)

Yield: 83% (light red oil). $^1$H NMR (CDCl$_3$, 400 MHz): δ 8.08 (d, 1H, J=1.6 Hz), 7.04 (d, 1H, J=1.6 Hz), 4.25 (m, 1H), 3.96 (m, 2H), 3.67 (m, 1H), 3.47 (m, 1H), 2.42 (s, 3H), 2.38 (m, 4H), 2.23 (m, 1H), 1.57 (m, 2H), 1.46 (m, 2H), 0.92 (t, 3H, J=7.2 Hz). $^{13}$C NMR (CDCl$_3$, 100 MHz): δ 152.3, 148.0, 143.1, 119.7, 118.8, 92.7, 77.4, 72.4, 57.1, 44.3, 30.6, 23.9, 22.0, 19.2, 19.1, 13.5. HRMS (ESI) m/z calcd for $C_{16}H_{22}N_2O$ (M+H)$^+$ 259.1810. found 259.1813; $[\alpha]_D^{24}$=−4.3 (c=0.77, CHCl$_3$). Anal. Calcd for $C_{16}H_{22}N_2O$. 0.625H$_2$O: C, 71.28; H, 8.69; N, 10.39. Found: C, 71.59; H, 8.56; N, 10.06.

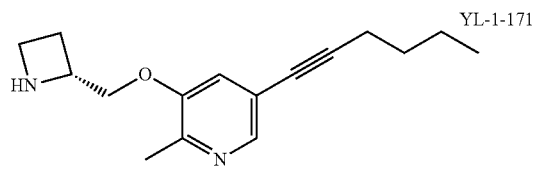 [SMILES: CCCCC#Cc1cnc(C)c(OC[C@H]2CCN2)c1]

(R)-3-(azetidin-2-ylmethoxy)-5-(hex-1-ynyl)-2-methylpyridine ((R)-15) (YL-1-171)

Yield: 75% (light red oil). $^1$H NMR (CDCl$_3$, 400 MHz): δ 8.07 (d, 1H, J=1.6 Hz), 7.04 (d, 1H, J=1.6 Hz), 4.24 (m, 1H), 3.94 (m, 2H), 3.66 (m, 1H), 3.45 (m, 1H), 2.41 (s, 3H), 2.36 (m, 3H), 2.24 (m, 2H), 1.56 (m, 2H), 1.45 (m, 2H), 0.92 (t, 3H, J=7.2 Hz). $^{13}$C NMR (CDCl$_3$, 100 MHz): δ 152.3, 148.0, 143.1, 119.7, 118.8, 92.7, 77.4, 72.5, 57.1, 44.3, 30.6, 24.0, 22.0, 19.2, 19.0, 13.5. HRMS (ESI) m/z calcd for $C_{16}H_{22}N_2O$ (M+H)$^+$ 259.1810. found 259.1816; $[\alpha]_D^{25}$=+10.8 (c=0.62, CHCl$_3$). Anal. Calcd for $C_{16}H_{22}N_2O$. 0.375H$_2$O: C, 72.49; H, 8.65; N, 10.57. Found: C, 72.72; H, 8.67; N, 10.43.

(S)-tert-butyl 2-((5-bromo-2-fluoropyridin-3-yloxy)methyl)azetidine-1-carboxylate ((S)-24)

To a mixture of the N-Boc protected alcohol (S)-1 (0.70 g, 3.7 mmol), 5-Bromo-2-fluoropyridin-3-ol (0.71 g, 3.7 mmol), and Ph$_3$P (1.10 g, 4.2 mmol) in anhydrous THF (70 mL) was added DEAD (2 mL of 40% solution in toluene) dropwise at 0° C. under nitrogen atmosphere. After stirring for 12 hours at 40° C., the solvent was removed under reduced pressure. The residue was purified by column chromatography on silica gel using a gradient of hexane-ethyl acetate (10:1 to 5:1) as the eluent to give the product (S)-24 (1.05 g) as a white solid. Yield: 79%. $^1$H NMR (CDCl$_3$, 400 MHz): δ 7.80 (t, 1H, J=2.0 Hz), 7.48 (dd, 1H, J=8.8, 2.0 Hz), 4.52 (m, 1H), 4.42 (m, 1H), 4.15 (dd, 1H, J=10.4, 2.4 Hz), 3.88 (t, 2H, J=10.4, 2.4 Hz), 2.34 (m, 2H), 1.42 (s, 9H).

(S)-tert-butyl 2-((2-fluoro-5-(6-hydroxyhex-1-ynyl) pyridine-3-yloxy)methyl)azetidine-1-carboxylate ((S)-25)

A mixture of (S)-24 (400 mg, 1.1 mmol), 5-Hexyn-1-ol (0.2 mL, 1.5 mmol), Pd(PPh$_3$)$_2$Cl$_2$ (42 mg, 0.06 mmol), CuI (23 mg, 0.12 mmol), PPh$_3$ (31 mg, 0.12 mmol) in Et$_3$N/DMSO (10 mL/1 mL) was heated to 50° C. overnight under a nitrogen atmosphere. The cooled mixture was taken up in ethyl acetate, and the organic phase was washed with water, brine, and then dried over Na$_2$SO$_4$. The extract was concentrated under reduced pressure, and the residue was purified by column chromatography on silica gel using a gradient of dichloromethane-ethyl acetate (1:4) as the eluent to give the product (S)-25 (398 mg) as a light yellow oil. Yield: 95%. $^1$H NMR (CD$_3$OD, 400 MHz): δ 7.72 (t, 1H, J=2.0 Hz), 7.57 (dd, 1H, J=9.6, 2.0 Hz), 4.50 (m, 2H), 4.18 (dd, 1H, J=10.8, 2.4 Hz), 3.86 (t, 2H, J=7.6 Hz), 3.61 (m, 2H), 2.47 (m, 2H), 2.35 (m, 2H), 1.69 (m, 4H), 1.40 (s, 9H).

(S)-tert-butyl 2-((2-fluoro-5-(6-(tosyloxy)hex-1-ynyl)pyridin-3-yloxy)methyl)azetidine-1-carboxylate ((S)-26)

To a stirred solution of (S)-25 (230 mg, 0.6 mmol) in dichloromethane (15 ml) was added DMAP (7 mg, 0.06 mmol), Et$_3$N (0.25 mL, 1.8 mmol), tosyl chloride (230 mg, 1.2 mmol) at 0° C. under a nitrogen atmosphere. The reaction mixture was stirred for 12 hrs at room temperature. The mixture was taken up in ethyl acetate, and the organic phase was washed with brine, and then dried over Na$_2$SO$_4$. The extract was concentrated under reduced pressure, and then residue was purified by column chromatography on silica gel using a gradient of hexane-ethyl acetate (4:1) as the eluent to give the product (S)-26 (298 mg) as a light yellow oil. Yield: 92%. $^1$HNMR (CDCl$_3$, 400 MHz): δ 7.80 (d, 2H, J=8.0 Hz), 7.74 (t, 1H, J=1.6 Hz), 7.34 (m, 3H), 4.51 (m, 1H), 4.39 (m, 1H), 4.14 (dd, 1H, J=10.4, 2.8 Hz), 4.09 (t, 2H, J=6.0 Hz), 3.88 (t, 2H, J=7.6 Hz), 2.45 (s, 3H), 2.40 (t, 2H, J=6.8 Hz), 2.33 (m, 2H), 1.82 (m, 2H), 1.65 (m, 2H), 1.42 (s, 9H).

(S)-tert-butyl 2-((2-fluoro-5-(6-fluorohex-1-ynyl) pyridin-3-yloxy)methyl) azetidine-1-carboxylate ((S)-27)

A mixture of (S)-26 (298 mg, 0.56 mmol), Kryptofix 2.2.2 (330 mg, 0.85 mmol), and KF (60 mg, 1.0 mmol) in dry THF (15 mL) was heated to reflux overnight under a nitrogen atmosphere. The cooled reaction mixture was concentrated under reduced pressure. The residue was purified by column chromatography on silica gel using a gradient of hexane-ethyl acetate (5:1) as the eluent to give the product (S)-27 (132 mg) as a light yellow oil. Yield: 62%. $^1$H NMR (CDCl$_3$, 400 MHz): δ 7.78 (s, 1H), 7.34 (dd, 1H, J=9.6, 1.6 Hz), 4.57 (t, 1H, J=6.0 Hz), 4.51 (m, 1H), 4.45 (t, 1H, J=6.0 Hz), 4.39 (m, 1H), 4.14 (dd, 1H, J=10.4, 2.8 Hz), 3.88 (t, 2H, J=7.6 Hz), 2.47 (t, 2H, J=6.8 Hz), 2.33 (m, 2H), 1.90 (m, 1H), 1.83 (m, 1H), 1.74 (m, 2H), 1.42 (s, 9H).

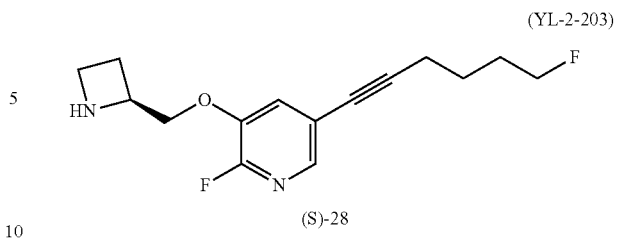

(YL-2-203)

(S)-28

(S)-3-(azetidin-2-ylmethoxy)-2-fluoro-5-(6-fluorohex-1-ynyl)pyridine di-trifluoroacetic acid ((S)-28)

To a stirred solution of (S)-27 (35 mg, 0.084 mmol) in dichloromethane (1 mL) was added trifluoroacetic acid (0.25 mL) dropwise at 0° C. under a nitrogen atmosphere. The reaction mixture was stirred for 3 h at room temperature. The solvent and excess TFA was then removed under reduced pressure. The residue was purified by column chromatography on silica gel using a gradient of CH$_2$Cl$_2$-methanol (5:1) as the eluent to give the product (S)-28 (31 mg) as a colorless oil. Yield: 72%. $^1$H NMR (CD$_3$OD, 400 MHz): δ 7.80 (t, 1H, J=1.6 Hz), 7.62 (d, 1H, J=9.6, 2.0 Hz), 4.86 (m, 1H), 4.54 (t, 1H, J=6.0 Hz), 4.42 (m, 3H), 4.07 (m, 2H), 2.67 (m, 2H), 2.50 (t, 2H, J=7.2 Hz), 1.80 (m, 4H). HRMS (ESI) m/z calcd for C$_{15}$H$_{18}$F$_2$N$_2$O (M+H)$^+$ 281.1465. found 281.1480.

Example 4

Cell Lines and Cell Culture

The cell lines expressing defined rat nAChR subtypes were established previously by stably transfecting HEK 293 cells with rat nAChR subunit genes. The cell line expressing human α4β2 nAChRs, YXα4β2H1, was established recently. These cell lines were maintained in minimum essential medium (MEM) supplemented with 10% fetal bovine serum, 100 units/mL penicillin G, 100 mg/mL streptomycin and selective antibiotics at 37° C. with 5% CO$_2$ in a humidified incubator. Fetal bovine serum was provided by Gemini Bio-Products (Woodland, Calif.). Tissue culture medium and antibiotics were obtained from Invitrogen Corporation (Carlsbad, Calif.), unless otherwise stated.

[$^3$H]-Epibatidine Radioligand Binding Assay.

Briefly, cultured cells at >80% confluence were removed from their flasks (80 cm$^2$) with a disposable cell scraper and placed in 10 mL of 50 mM Tris.HCl buffer (pH 7.4, 4° C.). The cell suspension was centrifuged at 10,000×g for 5 min and the pellet was collected. The cell pellet was then homogenized in 10 mL buffer with a polytron homogenizer and centrifuged at 36,000 g for 10 min at 4° C. The membrane pellet was resuspended in fresh buffer, and aliquots of the membrane preparation were used for binding assays. The concentration of [$^3$H]-epibatidine used was ~500 pM for competition binding assays. Nonspecific binding was assessed in parallel incubations in the presence of 300 µM nicotine. Bound and free ligands were separated by vacuum filtration through Whatman GF/C filters treated with 0.5% polyethylenimine. The filter-retained radioactivity was measured by liquid scintillation counting. Specific binding was defined as the difference between total binding and nonspecific binding. Data from competition binding assays were analyzed using Prism 5 (GraphPad Software, San Diego, Calif.). The K$_d$ values for [$^3$H]-epibatidine used for calculating $K_i$ values of nAChR subtypes were 0.02 nM for α2β2, 0.08 nM for α2β4, 0.03 nM for α3β2, 0.3 nM for α3β4, 0.04 nM for α4β2, 0.09 nM for α4β4, 1.8 nM for α7 and 0.05 for rat forebrain.

$^{86}Rb^+$ Efflux Assay.

Functional properties of compounds at nAChRs expressed in the transfected cells were measured using $^{86}Rb^+$ efflux assays as described previously. In brief, cells expressing human α4β2 or rat α3β4 nAChRs were plated into 24-well plates coated with poly-D-lysine. The plated cells were grown at 37° C. for 18 to 24 hour to reach 85-95% confluence. The cells were then incubated in growth medium (0.5 mL/well) containing $^{86}Rb^+$ (2 μCi/mL) for 4 hour at 37° C. The loading mixture was then aspirated, and the cells were washed four times with 1 mL buffer (15 mM HEPES, 140 mM NaCl, 2 mM KCl, 1 mM $MgSO_4$, 1.8 mM $CaCl_2$, 11 mM Glucose, pH 7.4). One mL of buffer with or without compounds to be tested was then added to each well. After incubation for 2 min, the assay buffer was collected for measurements of $^{86}Rb^+$ released from the cells. Cells were then lysed by adding 1 mL of 100 mM NaOH to each well, and the lysate was collected for determination of the amount of $^{86}Rb^+$ that was in the cells at the end of the efflux assay. Radioactivity of assay samples and lysates was measured by liquid scintillation counting. Total loading (cpm) was calculated as the sum of the assay sample and the lysate of each well. The amount of $^{86}Rb^+$ efflux was expressed as a percentage of $^{86}Rb^+$ loaded. Stimulated $^{86}Rb^+$ efflux was defined as the difference between efflux in the presence and absence of nicotine. For obtaining $EC_{50}$ and $E_{max}$ values, stimulation curves were constructed in which 8 different concentrations of a ligand were included in the assay. For obtaining an $IC_{50(10')}$ value, inhibition curves were constructed in which 8 different concentrations of a compound were applied to cells for 10 min before 100 μM nicotine was applied to measure stimulated efflux. $EC_{50}$, $E_{max}$ and $IC_{50(10')}$ values were determined by nonlinear least-squares regression analyses (GraphPad, San Diego, Calif.).

General Procedures for Effect on Alcohol Intake in Rats.

Adult male rats obtained from a colony of selectively-bred alcohol preferring rats (P rats) maintained at Indiana University School of Medicine. Rats were housed in cages that were fitted with two 100 mL Richter tubes for the recording of water and alcohol intake. Animals were kept under a constant room temperature of 22±1° C. and 12:12 light-dark cycle (7:00 a.m.-7:00 p.m. dark). Animals were fed 5001 Rodent Chow (Lab Diet, Brentwood, Mo., USA). All procedures were approved by the IACUC at Duke University Medical Center.

After a week of handling and habituation, rats were given free access to water in a graduated Richter tube for 1 day. Next, they were given free access only to a solution of 10% (v/v) alcohol for 3 consecutive days. Thereafter, rats were given free access to water and a solution of alcohol throughout the study. Water and alcohol intake were indexed by graduated Richter drinking tubes.

An acute study was conducted to determine a dose-response for compound (S)-15 (YL-1-127). After the establishment of a stable baseline for alcohol and water intake rats were injected subcutaneously with 0.33, 1 and 3 mg/kg of YL-1-127 or the same volume of the vehicle (1 mg/kg). Alcohol and water intake were measured at, 2, 4, 6 and 24 hr after the drug administration. The preference for alcohol solution, [(alcohol volume)/(alcohol+water volume)×100], was calculated for the same time points as alcohol and water intake. All animals (n=18) received all treatments following a crossover design with random assignment. The interval between injections was at least 3 days.

Solution of 10% (v/v) alcohol was prepared twice weekly from a solution of 200 proof ethanol mixed with tap water. Solutions of YL-1-127 were prepared weekly in 100 mM HCl solution and isotonic saline and was injected subcutaneously in a volume of 1 mL/kg.

The data were assessed by the analysis of variance with a between subjects factor of strain and a repeated measures factor of YL-1-127 dose. Significance was determined at $p<0.05$.

Abbreviations Used.

YL-2-203, compound (S)-28, (S)-3-(azetidin-2-yl-methoxy)-2-fluoro-5-(6-fluorohex-1-ynyl)pyridine di-trifluoroacetic acid; YL-1-127, compound (S)-15, (S)-3-(azetidin-2-ylmethoxy)-5-(hex-1-ynyl)-2-methylpyridine; nAChR, neuronal nicotinic acetylcholine receptors; CNS, central nervous system; VTA, ventral tegmental area; NAc, nucleus accumbens; [$^3$H], tritiated; P rats, alcohol-preferring rats; ADHD, Attention deficit hyperactivity disorder; $EC_{50}$, 50% agonism of the channel; $E_{max}$, maximal response; $IC_{50}$, 50% antagonism of the channel; binding affinity constant.

INCORPORATION BY REFERENCE

All of the U.S. patents and U.S. patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A compound represented by the formula:

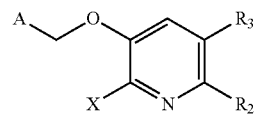

or a pharmaceutically acceptable salt thereof,
wherein, independently for each occurrence,
X is F, or Cl;
$R_2$ is H;
$R_3$ is

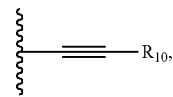

wherein $R_{10}$ is selected from the group consisting of H, hydroxy, halogen, and substituted or unsubstituted alkyl, aryl, and aralkyl;
wherein each substituent is independently selected from the group consisting of alkyl, alkenyl, alkynyl, alkoxy, amino, aryl, aralkyl, nitro, haloalkyl, heterocyclyl, halogen, and hydroxy; and A is

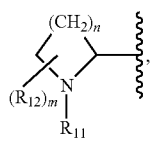

wherein,
m is 0, 1, 2, 3, 4, or
n is 1, 2, or 3;
R$_{11}$ is H, alkyl, or alkenyl; and
R$_{12}$ is alkyl, alkoxy, alkoxyalkyl, cyano, halogen, hydroxy, hydroxyalkyl, haloalkyl, —O—C(O)-alkyl, or —O-methanesulfonyl;
wherein the absolute stereochemistry at a stereogenic center may be R or S or a mixture thereof; and the stereochemistry of a double bond may be E or Z or a mixture thereof.

2. The compound of claim 1, wherein X is F.

3. The compound of claim 1, wherein R$_3$ is selected from the group consisting of

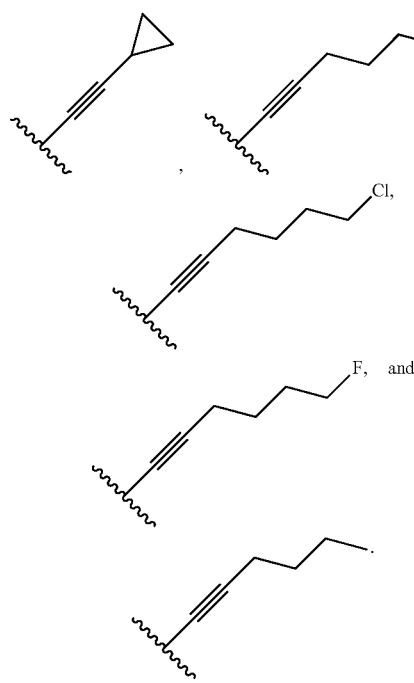

4. The compound of claim 1, wherein R$_{11}$ is H; and m is 0.

5. The compound of claim 1, wherein n is 1.

6. The compound of claim 1, wherein R$_{11}$ is H; m is 0; and n is 1.

7. The compound of claim 1, wherein X is F; R$_2$ is H; and R$_3$ is selected from the group consisting of

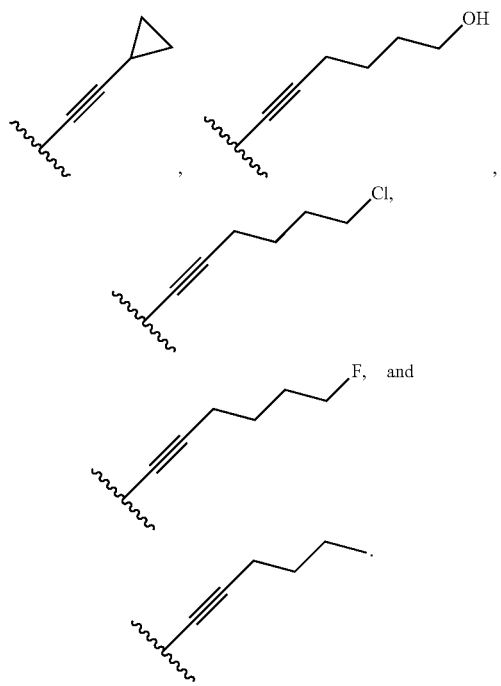

8. The compound of claim 7, wherein R$_{11}$ is H; m is 0; and n is 1.

9. The compound of claim 1, wherein the compound has the structure:

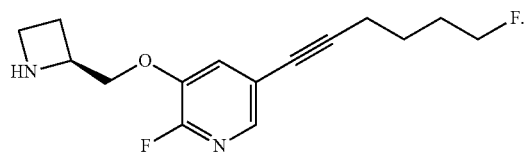 [SMILES: FCCCCC#Cc1cnc(F)c(OC[C@@H]2CCN2)c1]

10. A pharmaceutical composition, comprising a compound of claim 1; and a pharmaceutically acceptable excipient.

11. A method of modulating a nicotinic acetylcholine (Ach) receptor, comprising administering to a mammal in need thereof an effective amount of a compound of claim 1.

* * * * *